(12) United States Patent
Yamauchi et al.

(10) Patent No.: US 8,067,729 B2
(45) Date of Patent: Nov. 29, 2011

(54) MASS ANALYSIS DATA ANALYZING APPARATUS AND PROGRAM THEREOF

(75) Inventors: Kazuo Yamauchi, Kyoto (JP); Yoshitake Yamamoto, Kyoto (JP); Yoshikatsu Umemura, Kyoto (JP)

(73) Assignee: Shimadzu Corporation, Kyoto-shi, Kyoto (JP)

( * ) Notice: Subject to any disclaimer, the term of this patent is extended or adjusted under 35 U.S.C. 154(b) by 0 days.

(21) Appl. No.: 12/767,135

(22) Filed: Apr. 26, 2010

(65) Prior Publication Data

US 2010/0228498 A1    Sep. 9, 2010

Related U.S. Application Data

(62) Division of application No. 11/914,279, filed as application No. PCT/JP2006/308909 on Apr. 27, 2006, now abandoned.

(30) Foreign Application Priority Data

May 13, 2005    (JP) .................................. 2005-141845

(51) Int. Cl.
   *B01D 59/44*    (2006.01)
(52) U.S. Cl. .................. 250/282; 250/281; 436/173
(58) Field of Classification Search .................. 250/281, 250/282; 436/173; 702/22, 23, 27, 28, 30, 702/32

See application file for complete search history.

(56) References Cited

U.S. PATENT DOCUMENTS

| 2003/0109990 A1 | 6/2003 | Axelsson |
| 2005/0063864 A1* | 3/2005 | Sano et al. .................... 422/68.1 |
| 2009/0189063 A1* | 7/2009 | Sano et al. .................... 250/281 |

FOREIGN PATENT DOCUMENTS

| GB | 2 333 893 A | 8/1999 |
| JP | 2003-526793 A | 9/2003 |
| JP | 2005-91344 A | 4/2005 |
| JP | 2005-510732 A | 4/2005 |
| WO | 01/67485 A1 | 9/2001 |
| WO | 03/046577 A1 | 6/2003 |

OTHER PUBLICATIONS

D. Horn et al, "Automated Reduction and Interpretation of High Resolution Electrospray Mass Spectra of Large Molecules", Journal of the American Society for Mass Spectrometry, 2000, pp. 320-322, vol. 11.

(Continued)

*Primary Examiner* — Michael Maskell
(74) *Attorney, Agent, or Firm* — Westerman, Hattori, Daniels & Adrian, LLP

(57) ABSTRACT

In a mass analysis data analyzing apparatus, centroid data is used as mass spectrum data to be analyzed. First, peaks on the centroid data are specified in order of intensity as a standard peak for identifying an isotopic cluster. The isotopic cluster is detected by comparing an emerging pattern of peaks near the standard peak and an emerging pattern of peaks of an expected isotopic cluster in the case where each valence is assumed. The valence of the determined isotopic cluster is set as the valence of the peaks belonging to the isotopic cluster, and the peak at the forefront of cluster is selected as a monoisotopic peak. With such a mass analysis data analyzing apparatus, it is possible to determine the valence of each peak and identify the monoisotopic peak in a mass spectrum.

2 Claims, 4 Drawing Sheets

OTHER PUBLICATIONS

International Search Report of PCT/JP2006/308909, mailing date of Aug. 15, 2006.

M. Senko et al, "Determination of Monoisotopic Masses and Ion Populations for Large Biomolecules from Resolved Isotopic Distributions", Journal of the American Society for Mass Spectrometry, 1995, pp. 229-233, vol. 6.

Extended European Search Report dated Dec. 15, 2010, issued in corresponding European Patent Application No. 06745792.9.

Written Opinion of the International Searching Authority, issued in corresponding International Application No. PCT/JP2006/308909. English Translation.

* cited by examiner

MASS ANALYSIS DATA ANALYZING APPARATUS AND PROGRAM THEREOF

CROSS REFERENCE TO RELATED APPLICATION

This application is a divisional application of U.S. application Ser. No. 11/914,279 filed Nov. 13, 2007, which is a National Stage Application of PCT/JP06/308909 filed Apr. 27, 2006, which is hereby incorporated by reference in its entirety.

TECHNICAL FIELD

The present invention relates to a mass analysis data analyzing apparatus for determining the valence of each ion peak and identifying monoisotopic peaks in a mass spectrum by analyzing the data obtained by a mass analysis.

BACKGROUND ART

One conventional method for analyzing data obtained by a mass analysis is to use profile data, which shows a mass spectrum with an m/z value (mass-to-charge ratio) of ions detected in sequence and the detection intensity of them as data showing a mass spectrum as described in Non-Patent Documents 1 and 2. Profile data is a data form corresponding to raw data of a mass spectrometer. In the conventional mass analysis data analyzing method using the profile data, an isotopic cluster is first identified by analyzing the configuration of each peak on the profile data with a pattern recognition algorithm, and then, based on the result, the valence of each peak is determined and the monoisotopic peak is identified: where the isotopic cluster is a peak group consisting of a plurality of peaks which originate form ions having the same elemental composition yet have different m/z values depending on the difference of the isotopic composition of ions, and the monoisotopic peak is a peak of the ion which represents an isotopic cluster. Normally it is a peak of the ion consisting of the isotope having the largest natural abundance ratio.

[Non-Patent Document 1] *Journal of the American Society for Mass Spectrometry*, 2000, Vol. 11, pp. 320-332

[Non-Patent Document 2] *Journal of the American Society for Mass Spectrometry*, 1995, Vol. 6, pp. 229-233

DISCLOSURE OF THE INVENTION

Problem to be Solved by the Invention

Such a mass analysis data analyzing method as described earlier is used, for example, in "protein analyzing software" and the like for an offline-analysis of the data of a mass spectrometer after the completion of an analysis. An analysis of proteins by mass spectrometry generally includes the so-called MS/MS analysis (or MS$^n$ analysis), in which the capture and dissociation of ions corresponding to a particular peak are performed with a collision induced dissociation (CID) technique using a quadrupole ion trap (QIT). In this analysis, a function for dynamically selecting a precursor ion during an analysis (the "data dependent acquisition" or "DDA" function) is often required.

In an MS/MS analysis in general, an ion having a specific mass-to-charge ratio (m/z) in a target to be analyzed is first selected as a precursor ion, and then the ions produced by dissociating the precursor ion with CID (i.e. product ions) are mass-analyzed to obtain the information on the mass and chemical structure of the ions to be analyzed. Therefore, in order to realize the DDA function, a function for determining the valence of a peak which should be selected as a precursor ion from the mass spectrum and for automatically determining whether or not the peak is the monoisotopic peak is required in the course of analysis (i.e. online).

A technique for determining the valence of peaks and identifying monoisotopic peaks in a mass spectrum is realized, as described earlier, on conventional software and the like for an offline-analysis using profile data. However, such conventional analysis methods require a long analysis time and are not capable of realizing the DDA function, which is performed online during an analysis.

Hence, the present invention provides a mass analysis data analyzing apparatus capable of quickly determining the valence of each ion peak and identifying monoisotopic peaks in a mass spectrum.

Means for Solving the Problems

To solve the previously-described problem, the present invention provides a mass analysis data analyzing apparatus for determining a valence of each ion peak and identifying one or more monoisotopic peaks in a mass spectrum by analyzing mass spectrum data obtained by a mass analysis, including:

a) a centroid data creator for creating centroid data based on profile data obtained as the mass spectrum data; and b) a data analyzer for detecting an isotopic cluster in the mass spectrum based on an emerging pattern of peaks on the centroid data, determining a valence of peaks in the isotopic cluster based on the detection result, and identifying a monoisotopic peak of the isotopic cluster.

Here, "centroid data" is one of the data forms to show a mass spectrum, showing each peak in a mass spectrum with two values: an m/z value, which shows the centroid of the peak, and an area value of the peak.

In the mass analysis data analyzing apparatus according to the present invention, the data analyzer may preferably include:

c) a standard peak specifier for specifying a peak on the centroid data, in order of descending peak intensity, as a standard peak for identifying the isotopic cluster;

d) a pattern matcher for comparing an emerging pattern of peaks near the standard peak and an emerging pattern of peaks of an isotopic cluster within a predetermined valence range;

e) an isotopic cluster identifier for determining a valence of the isotopic cluster including the standard peak and for determining peaks belonging to the isotopic cluster, in the case where an emerging pattern of the standard peak and the peaks near it corresponds to the emerging pattern of peaks of the isotopic cluster as a result of a comparison by the pattern matcher;

f) a peak valence determiner for determining the valence of the isotopic cluster identified by the isotopic cluster identifier as a valence of the peaks belonging to the isotopic cluster; and g) a monoisotopic peak identifier for identifying a peak having the smallest mass-to-charge ratio in the isotopic cluster as a monoisotopic peak.

More preferably, the isotopic cluster identifier of the mass analysis data analyzing apparatus according to the present invention selects each candidate for the peaks belonging to the isotopic cluster by using a relative intensity to the standard peak or peaks already matched as the peaks belonging to the isotopic cluster when determining the peaks belonging to the isotopic cluster.

The program according to the present invention makes a computer functionate as an aforementioned mass analysis data analyzing apparatus.

Effect of the Invention

In the mass analysis data analyzing apparatus according to the present invention which has the aforementioned configuration, centroid data is used as mass spectrum data to be analyzed. In comparison to the conventional analysis method using profile data, therefore, the amount of the input data is much smaller and the algorithm of the pattern matching for identifying an isotopic cluster is simplified. This results in a significant reduction of the time required to identify an isotopic cluster, to determine the valence of each ion peak, and to identify a monoisotopic peak.

In the case where the mass analysis data analyzing apparatus according to the present invention includes the standard peak specifier, the pattern matcher, the isotopic cluster identifier, the peak valence determiner, and the monoisotopic peak identifier, the pattern matching regarding the near peaks is performed in order of descending peak intensity. In this case, it is possible to select each candidate for the peaks which should belong to the isotopic cluster, based on the relative intensity to the standard peak or to any other peaks which have already been matched as those belonging to the isotopic cluster when determining the peaks belonging to the isotopic cluster. In the case where the mass analysis data analyzing apparatus according to the present invention performs such selection, matching mistakes, e.g. an erroneous inclusion of noise peaks in an isotopic cluster, are reduced, and a high level of analysis accuracy is therefore ensured.

BRIEF DESCRIPTION OF THE DRAWINGS

FIG. 4(a) is an example of isotopic clusters identified as monovalent in a mass spectrum of PEG, and FIG. 4(b) is an example of an isotopic cluster identified as sexivalent in a mass spectrum of insulin.

EXPLANATION OF NUMERALS

10 . . . LCMS-IT-TOF Mass Spectrometer
20 . . . Dissociation/Detection Unit
21 . . . Ionization Unit
22 . . . Ion-Trap Mass Separation Unit
23 . . . Time-Of-Flight Mass Separation Unit
24 . . . Ion Detector
30 . . . Control/Process Unit
31 . . . Controller
32 . . . Data Processor

BEST MODE FOR CARRYING OUT THE INVENTION

Hereinafter, the best mode for carrying out the present invention is described using an embodiment.

Embodiment

The mass analysis data analyzing apparatus according to the present embodiment is a computer equipped with a program for analyzing mass-analysis data according to the present invention. The computer is included in a liquid chromatograph mass spectrometer 10 having an ion trap and a time-of-flight mass spectrometer (LCMS-IT-TOF, a registered trademark of Shimadzu Corporation). The mass analysis data analyzing apparatus operates as a part of the LCMS-IT-TOF 10. The computer may be incorporated in a part of the LCMS-IT-TOF 10 or may be a commercially produced personal computer.

Figure 1:
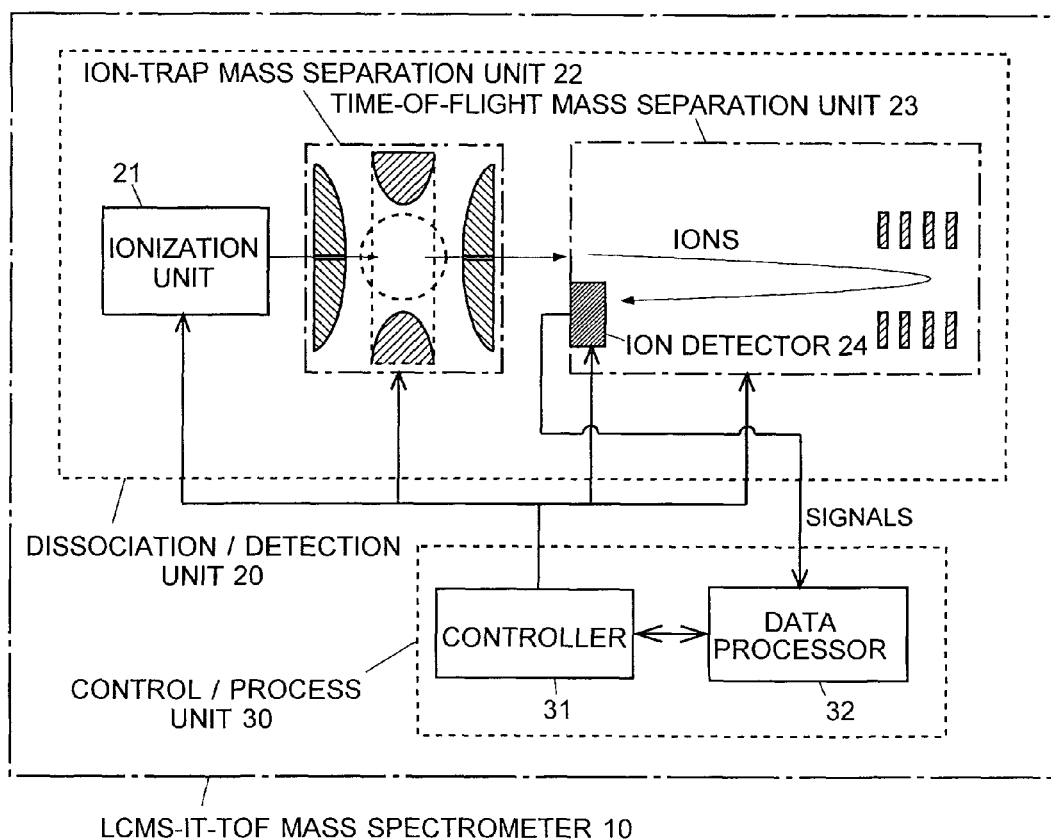
FIG. 1 is a schematic view of the mass analysis data analyzing apparatus according to an embodiment of the present invention.

The LCMS-IT-TOF 10 according to the present invention mainly consists of a dissociation/detection unit 20 and a control/process unit 30 as illustrated in FIG. 1. The dissociation/detection unit 20 includes an ionization unit 21 for ionizing a sample to be analyzed using the electrospray ionization (ESI) method, a quadrupole ion-trap mass separation unit 22 whose function is to select an ion having a predetermined m/z value as a precursor ion and to dissociate the precursor ion to produce product ions, a time-of-flight mass separation unit 23 for separating ions based on their m/z values, and an ion detector 24.

The control/process unit 30 is realized by a computer included in the LCMS-IT-TOF 10, and includes a controller 31 for controlling each part of the dissociation/detection unit 20, and a data processor 32 for performing a predetermined analysis by processing signals from the ion detector 24. The data processor 32 performs processing such as creating mass spectrum data, detecting an isotopic cluster, determining the valence of peaks, and identifying one or more monoisotopic peaks based on the mass spectrum data. These functions are achieved by the program according to the present invention, which is installed on the aforementioned computer.

Figure 2:
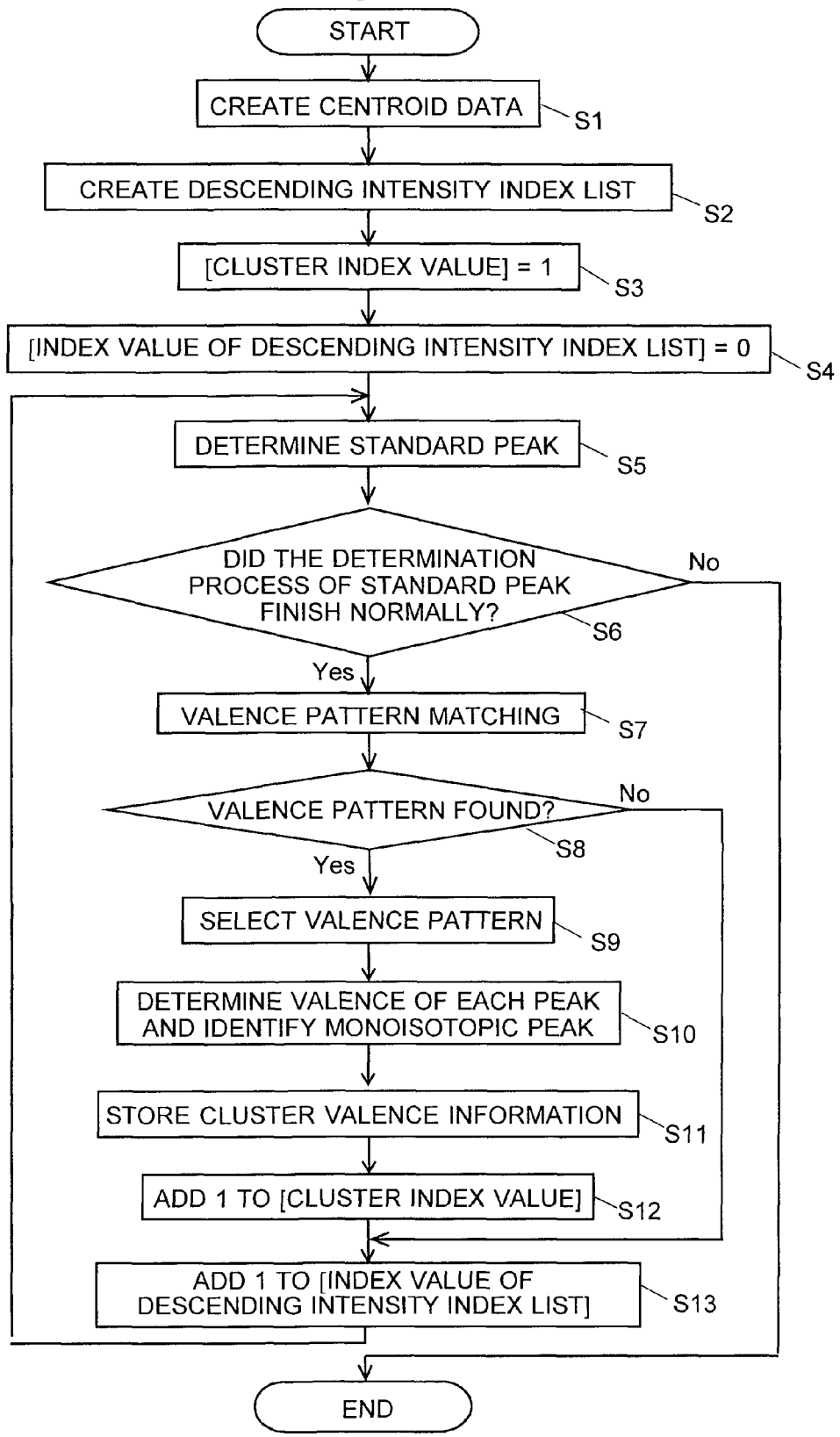
FIG. 2 is a flowchart showing the procedure of the data processing by the mass analysis data analyzing apparatus according to the present embodiment.
Figure 3:
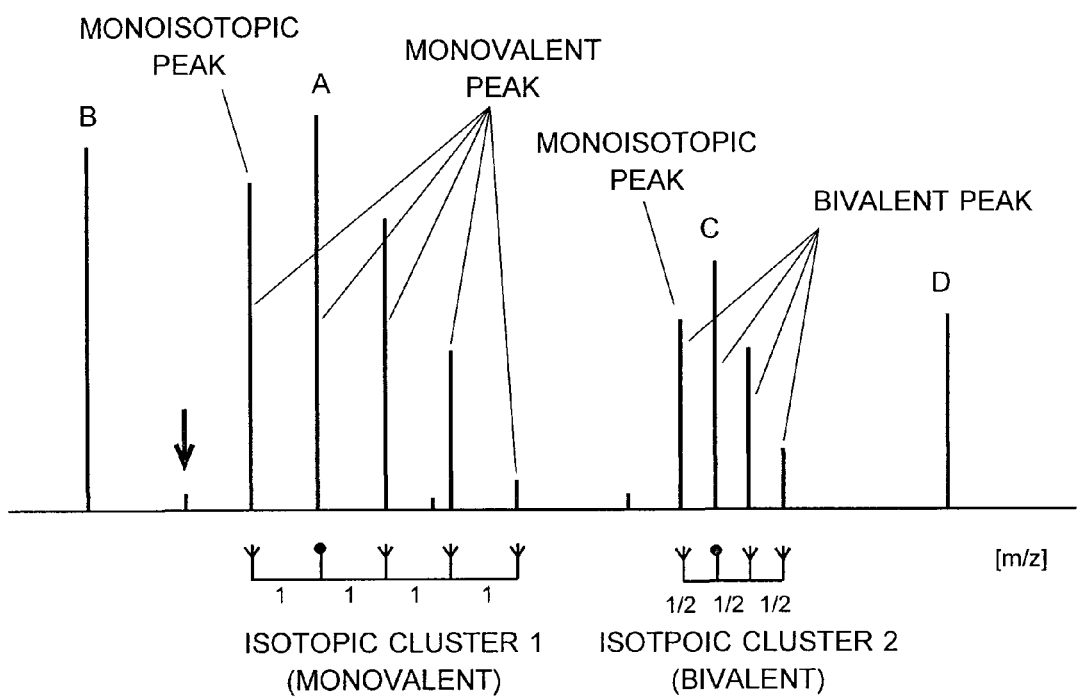
FIG. 3 is a conceptual diagram of a pattern matching process using centroid data by the mass analysis data analyzing apparatus according to the present embodiment.

A procedure of the data processing using the mass analysis data analyzing apparatus according to the present embodiment is hereinafter described with reference to the flowchart of FIG. 2 and the conceptual diagram of FIG. 3.

First, centroid data is created by converting the profile data of a mass spectrum created based on signals from the ion detector 24 (S1). The centroid data consists of a list of data structures each including the m/z value and intensity of each peak. For an isotopic peak, the data structure also includes the ID number of the isotopic cluster, the valence, and a flag indicating whether or not it is the monoisotopic peak. The index is sorted in order of the m/z value. Before the analysis is carried out, the aforementioned ID number and valence of the isotopic cluster, and the information on the monoisotopic peak are blank.

So as to access the centroid data in order of the intensity, an index list of each peak (descending intensity index list) is created (S2). In the index list, the peaks on the centroid data are listed in the descending order of peak intensity. Then, the ID number (cluster index value) of an isotopic cluster to be found from this point and the index value of the descending intensity index list are initialized (S3, S4). After this, on the centroid data, a peak is chosen as a candidate for the standard peak, i.e. a peak that serves as a basis for searching for the pattern of an isotopic cluster (S5). Since a peak to serve as a standard peak is selected in order of descending peak intensity, the base peak (a peak having the highest intensity among the measured peaks: peak A in FIG. 3) is chosen as the standard peak in the first process. In the processes after the first process, any peak identified as a peak belonging to the isotopic cluster in the previous processes will be kept from being selected as a standard peak.

Next, the peak pattern around the standard peak is analyzed to determine whether or not the peak pattern corresponds to the emerging pattern of the peaks of any of the isotopic clusters having different valence numbers (S7; this process is hereinafter called the "valence pattern matching").

At this point, as the parameters for the valence pattern matching, the following values are set:
(1) the range of valence for searching an isotopic cluster (default value: 1-10)
(2) the tolerance for the resolution for searching for the peaks belonging to an isotopic cluster (default value: ±50 ppm)
(3) the minimum value of the peak number to be considered to comprise an isotopic cluster (default value: 3)
(4) the maximum threshold for a cluster anterior matching, which will be described later in detail (default value: 0.3)
(5) the threshold for adjacent peak matching, which will be described later in detail (default value: 0.05)

The valence pattern matching includes the following steps: setting points at even intervals from the m/z value of the standard peak, the interval being determined for each isotopic cluster having a different valence number on the assumption that the isotopic cluster includes that standard peak; and checking whether or not a peak exists at each point (within the tolerance for the resolution specified by the parameter). For example, if a standard peak is included in a monovalent isotopic cluster, the peaks belonging to the isotopic cluster show a peak pattern with their m/z values different by one valence from each other; therefore the aforementioned interval is one as illustrated by the isotopic cluster 1 in FIG. 3. If a standard peak is included in a bivalent isotopic cluster, the peaks belonging to the isotopic cluster show a peak pattern with their m/z values different by ½ valence from each other; therefore the aforementioned interval is ½ as illustrated by the isotopic cluster 2 in FIG. 3.

As for the peaks anterior to the standard peak, i.e. anterior peaks, a threshold (the maximum value of this threshold is "the maximum threshold for a cluster anterior matching") of the relative intensity to the standard peak which is varied according to the mass value (the value of m/z value multiplied by an assumed valence z: unit [Da]) of the standard peak is set. A peak with its intensity equal to or below the threshold is removed from the candidates for the peaks belonging to the isotopic cluster in the matching process. For example, although the peak indicated by an arrow in FIG. 3 matches the peak pattern of the monovalent isotopic cluster which includes the standard peak A, its relative intensity to the standard peak A is below the threshold; therefore, it is determined as a noise to be removed from the candidates for the peaks belonging to the isotopic cluster 1.

In addition, maximum and minimum intensity values for a matching (the pair of these values is called "the threshold for adjacent peak matching") are determined according to the relative intensity to the peaks matched as those belonging to the isotopic cluster. Peaks having the intensity out of the maximum and minimum intensity values are removed from the candidates for the isotopic cluster peak. For example, if the relative intensity threshold value to the adjacent peak is 0.05, when the peak intensity of an adjacent peak is 100, the minimum value is 100×0.05=5, and the maximum value is 100/0.05=2000. Moreover, the peaks which are already identified as those belonging to an isotopic cluster are removed from the matching.

In the valence pattern matching, if there are two or more isotopic cluster valence patterns that have matched the peak pattern around the standard peak, an isotopic cluster valence pattern having the highest matching resolution (i.e. the standard deviation of the difference between the measured value and the predicted value in searching for each peak belonging to an isotopic cluster) is selected to identify the true isotopic cluster (S9). If there is only one valence pattern that has matched, that valence pattern is selected.

Next, the valence of the valence pattern selected in S9 is determined as the valence of each peak belonging to the identified isotopic cluster, and the peak at the forefront of the isotopic cluster is identified as the monoisotopic peak (S10). And, the ID number of the cluster, the valence, and the information on the monoisotopic peak of each peak belonging to the identified isotopic cluster are reflected as additional information in the aforementioned centroid data (S11).

Then, one is added to the cluster index value (S12) and also to the index value of the descending intensity index list (S13). And the processes of S5 through S13 are performed to all the peaks in the centroid data. If no peak pattern which matches as an isotopic cluster around a standard peak was found in the valence pattern matching (S7), as in the case of the standard peak B in FIG. 3, the processes of S9 through S12 are skipped and S13 is performed to determine the next standard peak (standard peak C in FIG. 3). If the index value of the descending intensity list is less than the number of the data on the centroid data in S6, it is determined that the determination process of the standard peak is normally finished and the analysis process is continued; otherwise, it is determined that it is finished as an abnormal end and the analysis process is terminated.

Figure 4:
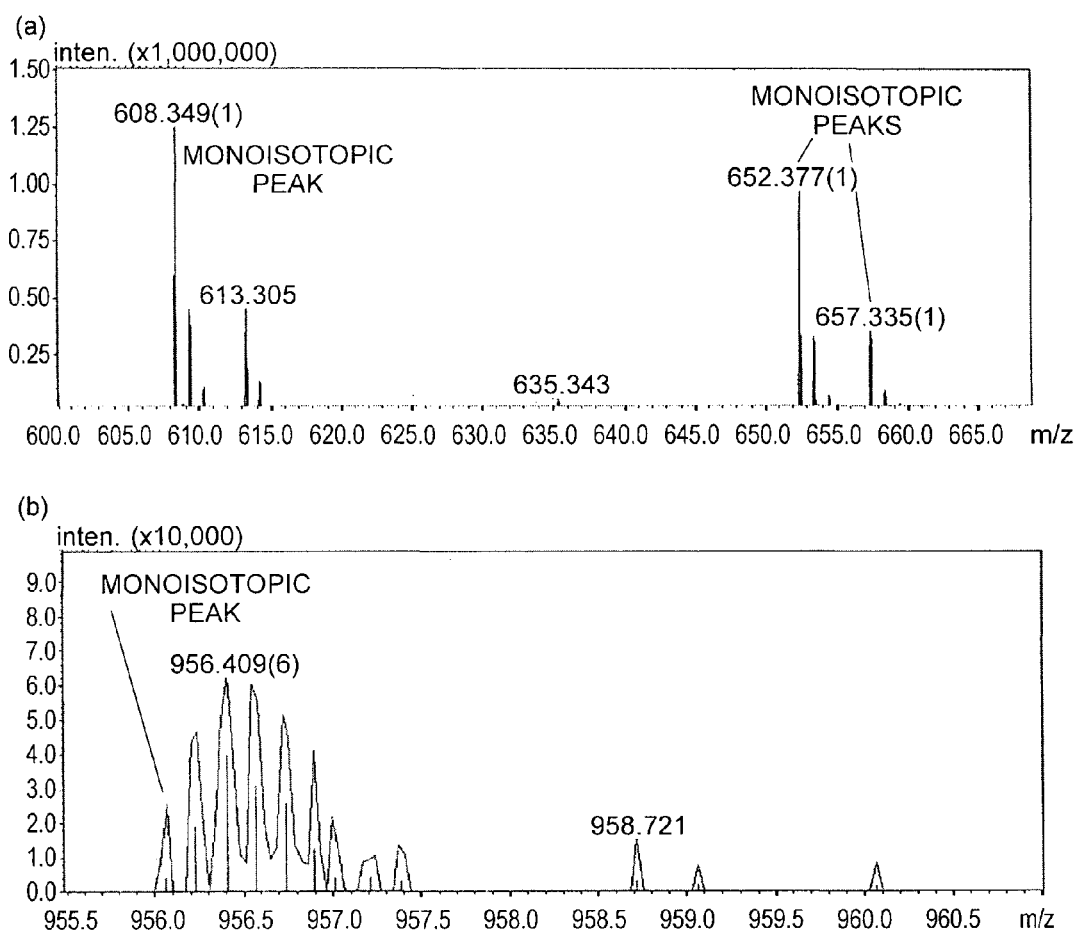
FIG. 4 shows examples of isotopic cluster peaks identified by the mass analysis data analyzing apparatus according to the present embodiment.

With these processes, in order of the intensity of peaks in a mass spectrum, a matching process of an isotopic cluster around each peak is sequentially performed to determine the valence of the peaks belonging to the identified isotopic cluster and locate the monoisotopic peak. FIG. 4 shows examples of isotopic peaks identified by the aforementioned process. The example of FIG. 4(*a*) shows isotopic clusters identified as monovalent in a mass spectrum of polyethylene glycol (PEG) as an analysis sample. The example of FIG. 4(*b*) shows an isotopic cluster identified as sexivalent in a mass spectrum of insulin as an analysis sample.

Experiment Example

Using a mass analysis data analyzing apparatus according to the present embodiment, an experiment was carried out to measure the time required for processing input data, which consisted of centroid data of a mass spectrum of myoglobin as an analysis sample (m/z=400-1500, number of peaks: 754). The result was 29.4 ms. The time required to convert profile data into the centroid data was 85.1 ms. Therefore, the total execution time for the automatic determination process of the valence of ion peaks, and of the monoisotopic peak in the mass spectrum was 85.1+29.4=114.5 ms. On the other hand, with an algorithm of a conventional art, it took approximately two hours to identify all the isotopic clusters in one mass spectrum. This confirms that the mass analysis data analyzing apparatus according to the present embodiment achieves the substantial reduction of analysis time. Furthermore, in order to realize the aforementioned DDA function, it is necessary to finish the determination of the valence of each peak and the identification of a monoisotopic peak of one mass spectrum on the order of 100 ms; the result of this experiment example confirmed that the mass analysis data analyzing apparatus according to the present embodiment is well capable of realizing the DDA function.

The mass analysis data analyzing apparatus according to the present invention may realize the DDA function by equipping a computer included in an apparatus having the MS/MS analysis function, such as the aforementioned LCMS-IT-TOF, with software for carrying out the processes of the detection of an isotopic cluster, determination of the valance of peaks, and the identification of a monoisotopic peak in a mass spectrum in accordance with such a data processing procedure as described earlier. However, it is not limited thereto; it may perform the data analysis online or offline on an external personal computer used in connection with various mass spectrometers and equipped with such software as previously described.

The invention claimed is:

1. A method for determining a valence of each ion peak and identifying one or more monoisotopic peaks in a mass spectrum by analyzing mass spectrum data obtained by a mass analysis, comprising the steps of:
   a) creating centroid data based on profile data obtained as the mass spectrum data;
   b) specifying a peak on the centroid data, in order of descending peak intensity, as a standard peak for identifying the isotopic cluster;
   c) comparing an emerging pattern of peaks near the standard peak and an emerging pattern of peaks of an isotopic cluster within a predetermined valence range, and determining, a valence of the isotopic cluster including the standard peak and for determining peaks belonging to the isotopic cluster, in a case where an emerging pattern of the standard peak and the peaks near it corresponds to the emerging pattern of peaks of the isotopic cluster as a result of a comparison;
   d) determining the valence of the isotopic cluster identified in the step c) as a valence of the peaks belonging to the isotopic cluster; and
   e) identifying a peak having a smallest mass-to-charge ratio in the isotopic cluster as a monoisotopic peak.

2. The method according to claim 1, wherein, in the step c), each candidate for the peaks belonging to the isotopic cluster is selected if a relative intensity to the standard peak or peaks already matched as the peaks belonging to the isotopic cluster is equal to or below a predetermined threshold when determining the peaks belonging to the isotopic cluster.

* * * * *